(12) United States Patent
Pecinovsky et al.

(10) Patent No.: US 8,507,052 B2
(45) Date of Patent: Aug. 13, 2013

(54) FERROELECTRIC LIQUID CRYSTAL MIXTURE WITH ORGANIC ION PAIR COMPOUND

(75) Inventors: Cory Pecinovsky, Longmont, CO (US); William Thurmes, Longmont, CO (US); Brion C. Koprowski, Longmont, CO (US)

(73) Assignee: Citizen Finetech Miyota Co., Ltd., Nagano (JP)

( * ) Notice: Subject to any disclaimer, the term of this patent is extended or adjusted under 35 U.S.C. 154(b) by 91 days.

(21) Appl. No.: 13/007,297

(22) Filed: Jan. 14, 2011

(65) Prior Publication Data

US 2011/0215274 A1    Sep. 8, 2011

Related U.S. Application Data

(60) Provisional application No. 61/310,112, filed on Mar. 3, 2010.

(51) Int. Cl.
*C09K 19/52* (2006.01)
*C09K 19/54* (2006.01)
*G09G 3/36* (2006.01)
*G02F 1/141* (2006.01)

(52) U.S. Cl.
USPC ............. 428/1.1; 252/299.01; 252/299.5; 345/87; 349/2

(58) Field of Classification Search
USPC .............. 252/299.01, 299.5; 428/1.1; 349/2; 345/87
See application file for complete search history.

(56) References Cited

U.S. PATENT DOCUMENTS

| | | | |
|---|---|---|---|
| 5,445,762 A | 8/1995 | Manero et al. | |
| 5,702,639 A | 12/1997 | Escher et al. | |
| 6,369,789 B1 | 4/2002 | Ulrich et al. | |
| 2002/0180925 A1 | 12/2002 | Tsuboyama et al. | |
| 2005/0253983 A1 | 11/2005 | Carson et al. | |
| 2006/0011887 A1 | 1/2006 | Kato et al. | |
| 2006/0091358 A1* | 5/2006 | Netland et al. | 252/299.2 |

FOREIGN PATENT DOCUMENTS

JP         08253766 A  * 10/1996

OTHER PUBLICATIONS

English translation by the computer for JP 08-253766 (1996), http://www4.ipdl.inpit.go.jp/Tokujitu/PAJdetail.ipdl?N0000=60&N0120=01&N2001=2&N3001=H08-253766.*

* cited by examiner

*Primary Examiner* — Shean C Wu (57) ABSTRACT

Ferroelectric liquid crystal compositions including organic ion pair compounds wherein image sticking is reduced or eliminated. Use of the ferroelectric liquid crystal compositions in a ferroelectric liquid crystal display device allows for rapid image refresh rates without required a DC-balancing algorithm. The organic ion pair compounds provide electrical resistivity values for the compositions that result in reduced image sticking when the compositions are used in FLC display devices.

37 Claims, 2 Drawing Sheets
(2 of 2 Drawing Sheet(s) Filed in Color)

FERROELECTRIC LIQUID CRYSTAL MIXTURE WITH ORGANIC ION PAIR COMPOUND

CROSS-REFERENCE TO RELATED APPLICATIONS

This application claims the priority of U.S. provisional application Ser. No. 61/310,112, filed Mar. 3, 2010, which is incorporated by reference herein in its entirety.

BACKGROUND

Ferroelectric liquid crystal displays offer great advantages in terms of quick response, the time needed for a change in orientation of the ferroelectric liquid crystal array being much shorter than the time needed for the change in a typical nematic liquid crystal. One great advantage of this quick response is that sequential coloring of pixels is possible at a refresh rate that facilitates color fusion, that is, the appearance to the human eye of the pixel as a single color rather than as rapidly sequentially changing colors. Sequential color also enables a higher resolution for a particular pixel size, as a single pixel can display all colors, rather than requiring three pixels, red, green and blue, to display a full color spectrum.

One phenomenon of liquid crystal displays such as those of the ferroelectric type is termed "image sticking," also known as "optical hysteresis" or "ghost images," referring to a residual image that is displayed on the screen persisting long after the driving voltages are removed from the ferroelectric liquid crystal (FLC) pixels. It is believed that ions present in the liquid crystal assembly can contribute to the image sticking problem. Charge densities are especially high in FLC devices because of the spontaneous polarization and the resulting internal electric fields. In sequential color ferroelectric liquid crystal on silicon (FLCOS) devices, a DC offset in the drive algorithm causes severe sticking, but operation in a DC balanced mode can reduce image sticking. DC balancing refers to the process wherein a voltage of inverse polarity is applied to a liquid crystal pixel immediately following application of a display voltage to assist in neutralizing residual electrical charges responsible for image sticking. However, this mode of operation requires that the LEDs supplying the light that is modulated by the FLCs be turned off during the balance phase when the inverse polarity voltage is applied, thereby reducing the light output of the device. See, for example U.S. Pat. No. 6,075,577.

Images are produced on an FLC display by applying a suitable pattern of voltages to the display's pixels and viewing the resultant pattern of FLC optical states using crossed polarizers. In standard video systems the displayed image changes at a rate of 60 frames per second. Under certain conditions an image can become "stuck" for a time; meaning that when subsequent images are displayed, the stuck image is superimposed on those later images.

Multiple mechanisms can contribute to image sticking: charge accumulation at FLC-alignment layer interfaces, changes in director orientation at the alignment layer, changes of pretilt, and perhaps changes in director gliding behavior. The mechanism addressed here is the accumulation of electrical charge at the surfaces of the FLC layer in response to applied voltages. Typically, as judged by the appearance of image sticking, the time constant for growth and decay of accumulated surface charge ranges from minutes to hours. To combat this problem FLC displays generally show each image and its complement in sequence (i.e. dark pixels made bright and vice versa). This ensures that the average voltage experienced by each pixel is zero, thus no charge should accumulate (assuming that the charge accumulation time is long compared to the frame period). The disadvantage of this scheme, referred to here as dc-compensation (see Clark, N. A., C. Crandall, M. A. Handschy, M. R. Meadows, R. M. Malzbender, C. Park, and J. Z. Xue, FLC microdisplays. Ferroelectrics, 2000, 246, p. 97-110), is that illumination must be turned off during display of the image complement so that it is not seen by viewers; the resulting 50% duty cycle reduces the effective display brightness by half. Duty cycle is defined as the proportion of time that the liquid crystal is driven so as to display the image. This is the maximum time that it is desirable to illuminate a display. For various reasons, it may not be desirable to illuminate the display for the entire period that the liquid crystal is driven so as to display the image.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 2 A-D show the images used in the evaluation of image sticking. Those images are an initial bright state, an initial checkerboard image, an initial dark state, and a post exposure dark state.

DETAILED DESCRIPTION

As used in the specification and the appended claims, the singular forms "a," "an" and "the" include plural referents unless the context clearly dictates otherwise.

All chiral, diastereomeric, racemic forms of a structure are intended, unless a particular stereochemistry or isomeric form is specifically indicated. Compounds used in embodiments of the present disclosed subject matter can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the disclosed subject matter.

A "cation" as is well known in the art refers to a molecular entity bearing one or more positive charges.

An "anion" as is well known in the art refers to a molecular entity being one or more negative charges.

An "organic ion pair compound", as the term is used herein, refers to a cation-anion pair in which at least one of the cation or anion comprises organic, that is, carbon-based, structural moieties. The organic structural moieties can include hydrocarbons and fluorocarbons, or molecules including carbon-hydrogen bonds, carbon-fluorine bonds, or both types of bonds. An organic ion pair includes a radical anion-radical cation pair formed in situ by electron transfer processes. Examples of organic cations include ammonium and phosphonium ions such as tetrabutylammonium and tetrabutylphosphonium, respectively. Other organic cations include tetrathiafulvene radical cations, imidazoliums, and the like. Examples of organic anions include organic sulfonates, fluorocarbonsulfonates, fluorocarbonsulfonylimides, dialkylenequinide radical anions and the like. Both ions need not be organic; for example organic ion pair compounds having an organic cation can have halide anions, tetrafluoroborate anions, and the like.

An "alkylammonium cation" as termed herein refers to an ammonium cation bearing at least one and as many as four alkyl groups. An "alkylarylammonium cation" refers to an ammonium cation bearing at least one alkyl and at least one aryl group. An "arylammonium cation" refers to an ammonium cation bearing at least one and as many as four aryl groups. A "quaternary ammonium" refers to any of the above or any ammonium ion wherein the quaternary nitrogen atom of the ammonium ion does not bear a hydrogen atom. A "long-chain alkyl" refers to a linear or branched alkyl group of about 12 to about 20 carbon atoms.

An "alkylphosphonium cation" as termed herein refers to a phosphonium cation bearing at least one and as many as four alkyl groups. An "alkylarylphosphonium cation" refers to a phosphonium cation bearing at least one alkyl and at least one aryl group. An "arylphosphonium cation" refers to a phosphonium cation bearing at least one and as many as four aryl groups. A "quaternary phosphonium" refers to any of the above or any phosphonium ion wherein the quaternary phosphorus atom of the phosphonium ion does not bear a hydrogen atom.

Embodiments of the present disclosed subject matter is directed to improved compositions for use in smectic liquid crystal displays, such as in ferroelectric liquid crystal displays. The compositions provide for reduced image sticking in the displays, which allows for faster refreshing of a liquid crystal display screen. The rapid refresh rate provides for higher quality images without undesired overlays of images previously displayed.

Embodiments of the present disclosed subject matter is directed in various embodiments to smectic liquid crystal compositions for use in a smectic liquid crystal display device, comprising an organic ion pair compound, the compound comprising an anion and a cation. In various embodiments, the smectic liquid crystal composition is a ferroelectric liquid crystal composition for use in a ferroelectric liquid crystal display device.

In various embodiments, the disclosed subject matter is directed to ferroelectric liquid crystal compositions including organic ion pair compounds, the compounds each comprising an anion and a cation, and to ferroelectric liquid crystal displays incorporating the compositions including organic ion pair compounds wherein image sticking is reduced compared to those compositions lacking the organic ion pair compounds. The present disclosed subject matter is also directed to methods for reducing image sticking in ferroelectric liquid crystal displays, and to methods of manufacture of liquid crystal compositions adapted for reducing image sticking in ferroelectric liquid crystal displays.

In various embodiments, the disclosed subject matter provides a composition adapted for use in a ferroelectric liquid crystal (FLC) display, comprising an organic ion pair compound. In various embodiments, the presence of the organic ion pair compound in the FLC composition used in a FLC display device, during operation of the display device when operating according to a DC-unbalanced algorithm, reduces image sticking relative to the composition lacking the organic ion pair compound. In various embodiments, the presence of the organic ion pair compound in the FLC composition used in a FLC display device, during operation of the display device when operating on a greater than 50% duty cycle, reduces image sticking relative to the composition lacking the organic ion pair compound.

In various embodiments, a concentration of the organic ion pair compound in the FLC composition of about 0.005-0.5 wt % can be present.

In various embodiments, the concentration of the organic ion pair compound in the FLC composition can be about 0.05 wt %-0.15 wt %.

In various embodiments, the organic ion pair compound comprises ion pairs in which at least one of the anion or the cation is an organic molecule. For example, the FLC composition can include an organic ion pair compound comprising a quaternary ammonium cation, for example, an alkylammonium cation or an arylammonium cation. More specifically, the alkylammonium cation can be a tetrabutylammonium cation or a long-chain alkyl ammonium cation. Alternatively, the FLC composition can include an organic ion pair compound comprising a quaternary phosphonium cation, for example, a alkylphosphonium or a alkylarylphosphonium cation.

In various embodiments, the organic ion pair compound can comprise radical cation-radical anion pair. For example, the organic ion pair compound can be the radical transfer reaction product of tetracyanoquinonedimethide and tetrathiafulvene, such that the tetrathiafulvene radical cation is the cationic component of the ion pair and the tetracyanoquinonedimethide radical anion is the anionic component of the ion pair.

In various embodiments, the organic ion pair compound can comprise a cation comprising a heterocyclic ring. More specifically, the heterocyclic ring can contain a quaternarized nitrogen atom. For example, the cationic heterocyclic ring can be a quaternatized imidazolium.

In various embodiments, the anionic component of the organic ion pair compound can be organic, in which case the cationic component can be organic or inorganic, or the anionic component can be inorganic, in which case the cationic component is organic. For example, the anionic component can be an organic sulfonate anion, such as an alkylsulfonate or a fluoroalkylsulfonate anion. Alternatively, the anionic component of the organic ion pair compound can be a nitrogen anion, such as a fluoroalkylsulfonylimide anion. Or, the anionic component of the organic ion pair compound can be a phosphinate anion, or can be a tetrafluoroborate or a tetraarylboride anion, or can be a halide anion.

The resistivity of the FLC composition of various embodiments of the disclosed subject matter including the organic ion pair compound can be a factor in controlling the decrease in image sticking observed upon use of a composition of the disclosed subject matter compared to an art FLC composition lacking the organic ion pair compound. Although not wishing to be bound by theory, the inventors herein believe that the flow of electrical current through the FLC display device brought about by the presence of a suitable concentration of an organic ion pair compound, thus producing a suitable resistance in a specific FLC display device, may at least in part account for the favorable reduction in image sticking using the compositions and methods of the disclosed subject matter. The resistivity of any particular composition of the disclosed subject matter is a function, inter alia, of the concentration of the organic ions in the FLC composition, the mobility of the organic ions in the FLC composition, and possible phase separation (precipitation) of the organic ion pair compounds from the FLC composition.

For example, for a 1 $cm^2$ FLC cell adapted for use in a FLC display device, the capacitance of a generic polyimide align- ment layer having a thickness of ~20 nm and a dielectric constant of ~4 is approximately 200 nC/cm². For switching rate $t_{SW}=1/720$ seconds (a typical FLCOS frame period) and eye image fusion rate $t_{vision}=1/30$ seconds this requires a cell resistance of about 14 kΩ to about 0.3 MΩ. For a typical FLC layer whose thickness is on the order of 1 μm, the resistivity of the FLC should correspondingly be in the range 140 MΩ·cm to about 3 GΩ·cm. In practice the $t_{vision}$ limit of $1/30^{th}$ seconds may be excessively stringent, i.e. it can be visually acceptable for image sticking to persist for a larger fraction of a second so that resistivities as large as 20 GΩ·cm may be acceptable. Accordingly, in such embodiments, the resistivity of the composition including the organic ion pair compound can be in the range of about 140 MΩ·cm to about 20 GΩ·cm, such that electrical resistance of the FLC composition in the above-described device can be within the range of about 14 kΩ to about 2 MΩ. The concentration of the organic ion pair compound in the FLC composition suitable to achieve such resistivities for the composition and resistances for the FLC display device as described can be about 0.005 wt % to about 0.5 wt %. More specifically, the concentration of the organic ion pair compound in the FLC composition can be about 0.05 wt % to about 0.15 wt %.

It is within ordinary skill to adjust a wt % of an organic ion pair compound in any particular FLC composition within these approximate ranges to achieve a suitable composition resistivity as defined above, such that the device displays a suitable resistance as defined above for a display device of a surface area of 1 cm2. It is within ordinary skill to calculate from the specified resistivity values the target resistance for a FLC display device of any area or layer thickness therefrom.

In various embodiments, the organic ion pair compound can be of any of the following specific compounds:

or any mixture thereof.

In various embodiments, the organic ion pair compound can comprise an ion pair compound comprising any anion of any of the compositions disclosed herein in combination with any of cation disclosed herein, provided the cation and the anion together have sufficient solubility in the liquid crystal composition such that resistivity of the composition including the organic ion pair compound is in the range of about 140 MΩ·cm to about 20 GΩ·cm In various embodiments, the present disclosed subject matter provides a ferroelectric liquid crystal (FLC) display device comprising any of the FLC compositions of the disclosed subject matter as described above. The display device can contain within the liquid crystal cell a ferroelectric liquid crystal display composition, for example Chisso CS 1024, as are well known in the art, but containing an organic ion pair compound as described herein.

In various embodiments, the display can operate on a non-DC balanced algorithm with a greater than 50% duty cycle with a lower level of image sticking relative to a comparable display lacking the organic ion pair compound. The inventive FLC composition serves to reduce image sticking to a degree such that a neutralizing voltage need not be applied to relax the liquid crystal to its transmissive state. In various embodiments, the FLC display can be brighter when in operation than a comparable display lacking the organic ion pair compound and operating on a duty cycle of 50% or less would be. The enhanced brightness of FLC display devices available through the use of the inventive compositions is an outstanding advantage of the present disclosed subject matter.

In various embodiments, a FLC display device of the disclosed subject matter can comprise an ferroelectric liquid crystal layer having a composition wherein resistivity of the composition including the organic ion pair compound is in the range of about 140 MΩ·cm to about 20 GΩ·cm.

In various embodiments, a FLC display device of the disclosed subject matter can comprise an ferroelectric liquid crystal layer having a composition wherein resistivity of the composition including the organic ion pair compound is in the range of about 140 MΩ·cm to about 3 GΩ·cm.

In various embodiments of a FLC display device of the disclosed subject matter, image sticking persists for less than about $1/30^{th}$ of one second. In other embodiments, image sticking persists for less than about $1/12^{th}$ of one second.

In various embodiments, a FLC display device of the disclosed subject matter comprises any of the FLC compositions of the disclosed subject matter, including any of the specific organic ion pair compounds disclosed above.

In various embodiments, the present disclosed subject matter provides a method of reducing image sticking in a ferroelectric liquid crystal composition used in a ferroelectric liquid crystal display device, comprising adding an organic ion pair compound to the composition. For example, the organic ion pair compound can be present at about 0.005 wt % to about 0.5 wt %. More specifically, the organic ion pair compound can be present at about 0.05 wt % to about 0.15 wt %.

The organic ion pair compounds were evaluated as additives at the 0.1 wt % level in a known FLC liquid crystal composition, Chisso CS 1024. The additives were evaluated for producing a reduction in image sticking in a FLC display device as described below.

Nissan RN-1175 and RN-1744 polyimide alignment layers were constructed with 0.78 um spacers. These cells were vacuum filled (110C) with Chisso FLC mixture CS-1024 and with an exemplary composition of the present disclosed subject matter of CS-1024 containing 0.15 wt % tetrabutylammonium perfluorobutanesulfonate, termed MX13135. Upon cooling to the C phase, both cells adopted a uniform C2 chevron structure. The magnitude of image sticking was then evaluated on each part by displaying a checkerboard with a DC-imbalanced drive scheme. Half of the checkerboard ("black") was being driven by a 720 Hz square wave with a 25% high field. The other half ("white") was with a 75% high field. The checkerboard was left on the display for 5 minutes, followed by an all black field (25% high field). A photograph was taken within 2 s of changing from the checkerboard pattern, and this image was used to calculate the magnitude of image sticking. Addition of the 0.15 wt % of tetrabutylammonium nonafluorobutanesulfonate (PFAS) to CS-1024 to provide composition MX13135 resulted in a 4× improvement in the image sticking magnitude.

Figure 1:
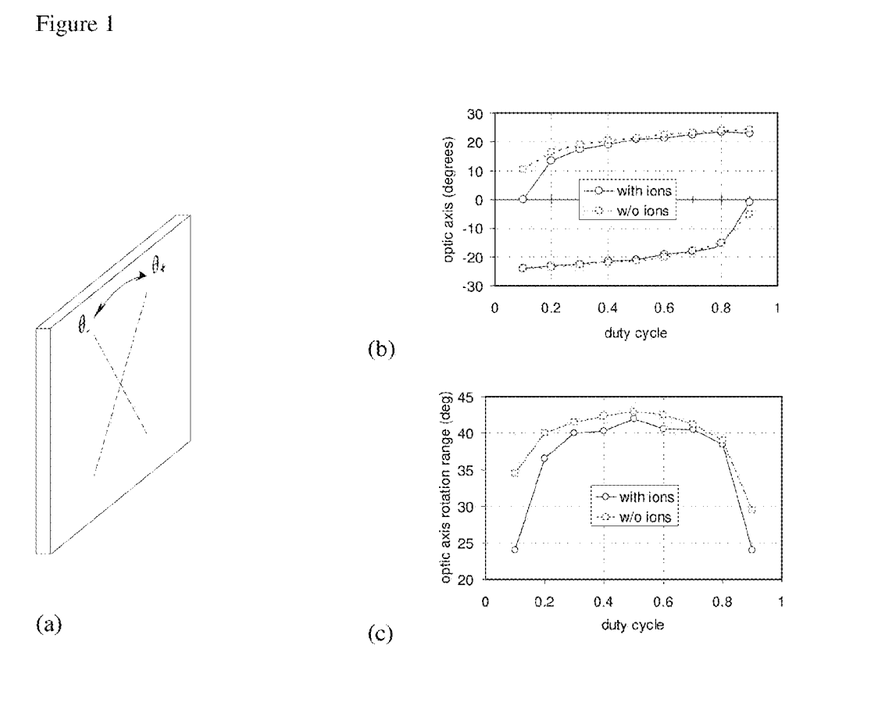
FIG. 1 shows data comparing FLC optic axis rotation with and without added ionic conductivity. One cell was filled with the FLC MX13058 (no added ionic conductivity), the other was filled with MX12918 (an ion-doped version of MX13058).

FIG. 1(a) shows data comparing FLC optic axis rotation with and without added ionic conductivity. One cell was filled with the FLC MX13058 (no added ionic conductivity), the other was filled with MX12918 (an ion-doped version of MX13058). Both cells were FLCOS dummies. FLCOS dummies are similar in physical structure to live microdisplays, but without the CMOS VLSI circuitry normally present in the silicon. The cells were driven with waveforms with high fields ranging from 10% to 90%, an amplitude of ±1.8V, at a frequency of 720 Hz (a typical FLCOS microdisplay frame rate). FLC optic axis positions for positive and negative drive voltages, respectively, were measured just before each voltage transition to allow maximum settling time.

FIG. 1(b) shows plots of θ+ and θ− vs. high field for cells with and without added ionic conductivity, FIG. 1(c) shows change of θ vs. high field to better highlight differences between the two cases. As expected, the ion-doped FLC shows reduced optic axis rotation compared to the undoped FLC as extremes of high field are approached. The effect of conductivity on optic axis position is not extreme in this example because the dopant concentration was kept to the minimum necessary to have a beneficial degree of perceived image sticking reduction and not interfering with full switching of the FLC.

Table 1, below, shows exemplary organic ion pair compounds used in FLC compositions of the disclosed subject matter and the properties of FLC displays similar to those described for FIG. 1B, but containing about 0.1 wt % of the specified component in place of the tetrabutylammonium perfluorobutanesulfonate. The first column shows the structure of the organic ion pair compound tested; the second column states the solubility of the compound in the FLC mixture, e.g., Chisso CS1024. The third column gives a qualitative evaluation of the degree of image sticking as evaluated by procedures given below in the Examples, and the fourth column characterizes the conductivity (i.e., the inverse of the resistivity) with respect to the values for resistivity of a composition of the disclosed subject matter and resistance of a FLC display device cell using a composition of the disclosed subject matter, as described above.

TABLE 1

Exemplary Organic Ion Pair Compounds

| Structure | Solubility in FLC | Image sticking properties | Conductivity at ~0.1 wt % |
|---|---|---|---|
| Bu-N⁺(Bu)(Bu)Bu  ⁻O-S(=O)(=O)-C₈F₁₇ | Good | Good | Within useful range |
| 1-butyl-3-(tridecafluorohexyl)imidazolium  PF₆⁻ | Unknown | Poor | Apparently too low |
| C₆H₁₃-P⁺(C₆H₁₃)(C₆H₁₃)-C₁₄H₂₉   bis(2,4,4-trimethylpentyl)phosphinate | Good | Good | Within useful range |
| C₁₈H₃₇-N⁺(C₁₈H₃₇)(C₁₈H₃₇)-C₁₈H₃₇  Br⁻ | Believed poor | Good | Within useful range |
| R₄N⁺  BF₄⁻ | Poor | Poor | Apparently too low |
| C₁₆H₃₃-S(=O)(=O)-O⁻  Na⁺ | Poor | Poor | Apparently too low |

TABLE 1-continued

Exemplary Organic Ion Pair Compounds

| Structure | Solubility in FLC | Image sticking properties | Conductivity at ~0.1 wt % |
|---|---|---|---|
| [($C_{12}H_{25}$)$_4$N$^+$] [B(4-Cl-C$_6$H$_4$)$_4$]$^-$ | Good | Good | Too high |
| [($C_{12}H_{25}$)$_4$N$^+$] Br$^-$ | Poor | Good | Within useful range |
| [Bu$_4$N$^+$] Cl$^-$ | Unknown | Poor | Apparently too low |
| [Bu$_4$N$^+$] [N(SO$_2$CF$_3$)$_2$]$^-$ | Good | Good | Too high |
| [1-ethyl-3-methylimidazolium]$^+$ [N(SO$_2$CF$_3$)$_2$]$^-$ | Good | Good | Too high |
| [($C_8H_{17}$)$_4$N$^+$] Br$^-$ | Poor | Good | Within useful range |
| [($C_{12}H_{25}$)$_4$N$^+$] Cl$^-$ | low | Good | Within acceptable range |
| [4-MeC$_6$H$_4$SO$_3$]$^-$ [Bu$_4$N$^+$] | Unknown | Poor | Unknown |

TABLE 1-continued

Exemplary Organic Ion Pair Compounds

| Structure | Solubility in FLC | Image sticking properties | Conductivity at ~0.1 wt % |
|---|---|---|---|
|  | Good | Good | Within acceptable range |
|  | Unknown | Poor | Unknown |
|  | Poor | Good | Within acceptable range |
|  | Poor | Good | Too high |
|  | Poor | Good | Within acceptable range |
|  | Very low | | |
|  | unknown | good | Within useful range |
| ⊕N(C$_{12}$H$_{25}$)$_4$ CF$_3$CF$_2$CF$_2$CF$_2$SO$_3$⊖ | Unknown | Good | Within useful range |
| ⊕N(C$_{18}$H$_{37}$)$_4$ CF$_3$CF$_2$CF$_2$CF$_2$SO$_3$⊖ | Good | Good | Within useful range |
|  | Low | Poor | Too low |
|  | unknown | Poor | Too low |

TABLE 1-continued

Exemplary Organic Ion Pair Compounds

| Structure | Solubility in FLC | Image sticking properties | Conductivity at ~0.1 wt % |
|---|---|---|---|
| (C$_{18}$H$_{37}$)$_4$N$^+$ / BF$_4^-$ | Low | Good | Within useful range |
| Bis(1,3-dithiol-2-ylidene)/TCNQ-type structure (tetrathiafulvalene with dicyanomethylene quinoid) | Unknown | Good* (high adsorption coeff.) | Unknown |
| (C$_{18}$H$_{37}$)$_4$N$^+$ / C$_{16}$H$_{33}$—SO$_3^-$ | TBD | TBD | TBD |
| Alkylphosphonate anion / (C$_{18}$H$_{37}$)$_4$N$^+$ | TBD | TBD | TBD |

The stated image sticking properties and conductivities in Table 1 are related to the effect of the organic ion pair compound at about 0.1 wt % of the FLC composition. It is within ordinary skill, knowing the target composition resistivities/resistances of FLC layers in display devices, to adjust the concentration of any particular agent to provide for a suitable resistivity value, provided the particular organic ion pair compound has sufficient solubility in the FLC composition to provide that value. Due to differing molecular weights of the various organic ion pair compounds tested, a 0.1 wt % concentration of each results in varying molar concentrations of the ion pair compounds in the FLC composition.

EXAMPLES

The ferroelectric liquid crystal medium used in the evaluation examples herein was Chisso CS1024. Other suitable compositions are described in the following patents, by the inventors herein, which are incorporated by reference herein in their entireties:
U.S. Pat. Nos. 7,425,281, 6,838,128, 6,737,124, 6,759,101, 6,783,812, and 5,585,036.

For evaluation of compositions of the disclosed subject matter with respect to reduction in image sticking, symmetric cells consisting of Nissan RN-1175 and RN-1744 polyimide alignment layers were constructed with 0.78 µm spacers. These cells were vacuum filled (110C) with Chisso FLC mixture CS-1024 containing about 0.1 wt % of the organic ion pair compound under evaluation. The magnitude of image sticking was then evaluated on each part by displaying a checkerboard with a DC-imbalanced drive scheme as described below.

The evaluation of image sticking is carried out using an automated image sticking analysis system having two principle components. The first component exposes the device to the test condition and acquires the image data for analysis. The second component uses the acquired images to determine the magnitude of the residual image across the display.

Figure 2:
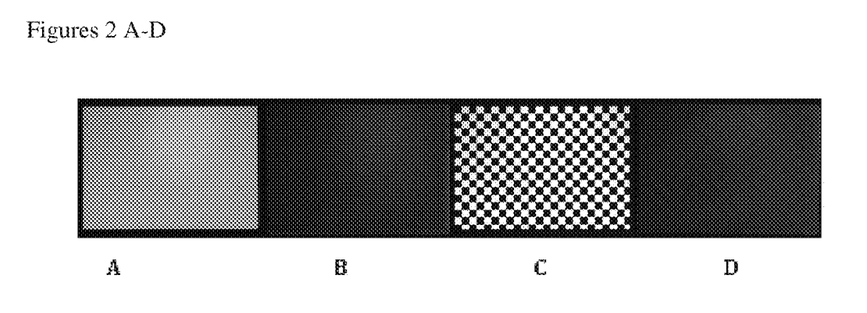

During the test, the device is exposed to the following conditions. First, the device is driven with white noise for one minute DC balanced while the LED illumination system is brought into thermal equilibrium. After the LED equilibrium period, the device is set to drive the desired non-DC balanced algorithm. Three images are acquired to define the pre-exposure state of the display. The three images are a bright state, a dark state, and a checkerboard pattern. The checkerboard pattern is the same pattern that is used during the exposure. After data for the initial state of the display is acquired, the device displays the checkerboard pattern for a five-minute dwell. This dwell is the test exposure condition. After the dwell, the device is switched to a dark state pattern and image data is collected. At the completion of the experiment sequence four images are available and used for the analysis step. Those images are an initial bright state, an initial checkerboard image, an initial dark state, and a post exposure dark state as shown in FIG. 2 A-D.

For each image acquisition step in the process camera integration time and the number of image averages are selectable. For a typical experiment, bright state integration times are 200 ms and dark state integration times are 1200 ms. Additionally, typically the average of 10 images is used for each acquisition.

Figure 3:
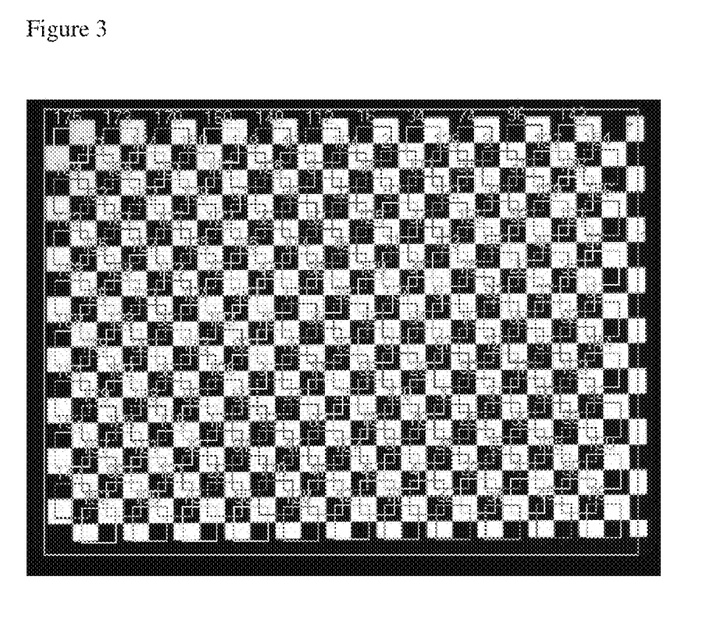
FIG. 3 shows the checkerboard pitch used during the test exposure defines these analysis regions.

The image sticking analysis component uses the acquired images to determine the regional change in dark state brightness with respect to the pre-exposure dark state brightness. First, the acquired bright state image is used to compute any rotation in the active area of the display under test. Secondly, the pre-exposure checkerboard image is used to reference regions across the display for analysis after exposure. Typically, 176 analysis regions across the display are used. The checkerboard pitch used during the test exposure defines these analysis regions are as shown in FIG. 3.

In each analysis region, the software determines the difference in dark state brightness between regions in the checkerboard that were exposed bright and regions in the checkerboard that were exposed dark. Those differences are then compared to the display dark value in the analysis region prior to the test exposure. Consequently, for each of the 176 analysis regions, a value for image sticking as a percentage of the dark state is computed. Using the location data in conjunction with the image sticking magnitude the system can spatially resolve image-sticking variations across the panel. Additionally, basic statistics for the population of analysis regions are calculated to compare the performance across samples.

All patents and publications referred to herein are incorporated by reference to the same extent as if each individual publication was specifically and individually indicated to be incorporated by reference herein in its entirety.

The terms and expressions which have been employed are used as terms of description and not of limitation, and there is no intention in the use of such terms and expressions of excluding any equivalents of the features shown and described or portions thereof, but it is recognized that various modifications are possible within the scope of the disclosed subject matter claimed. Thus, it should be understood that although the present disclosed subject matter has been specifically disclosed by preferred embodiments and optional features, modification and variation of the concepts herein disclosed may be resorted to by those skilled in the art, and that such modifications and variations are considered to be within the scope of this disclosed subject matter as defined by the appended claims.

What is claimed is:

1. A smectic liquid crystal composition for use in a smectic liquid crystal display device, comprising a ferroelectric liquid crystal (FLC) composition for use in a ferroelectric liquid crystal display device, comprising, an organic ion pair compound comprising an anion and a cation.

2. The composition of claim 1 wherein the presence of the organic ion pair compound in the FLC composition used in a FLC display device, during operation of the display device when operating according to a DC-unbalanced algorithm, reduces image sticking relative to the composition lacking the organic ion pair compound.

3. The composition of claim 1 wherein the presence of the organic ion pair compound in the FLC composition used in a FLC display device, during operation of the display device when operating on a greater than 50% duty cycle, reduces image sticking relative to the composition lacking the organic ion pair compound.

4. The composition of claim 1 wherein a concentration of the organic ion pair compound in the composition is about 0.005 wt % to about 0.5 wt %.

5. The composition of claim 1 wherein a concentration of the organic ion pair compound in the composition is about 0.05 wt % to about 0.15 wt %.

6. The composition of claim 1 wherein the organic ion pair compound comprises a alkylammonium cation or an arylammonium cation.

7. The composition of claim 6 wherein the alkylammonium cation is a tetrabutylammonium cation or a long-chain alkyl ammonium cation.

8. The composition of claim 1 wherein the organic ion pair compound comprises a alkylphosphonium or a alkylarylphosphonium cation.

9. The composition of claim 1 wherein the organic ion pair compound comprises a radical cation-radical anion pair.

10. The composition of claim 1 wherein the organic ion pair compound comprises an cation comprising a heterocyclic ring.

11. The composition of claim 10 wherein the heterocyclic ring is an imidazolium.

12. A smectic liquid crystal composition for use in a smectic liquid crystal display device, comprising an organic ion pair compound comprising an anion and a cation, wherein the organic ion pair compound comprises a fluoroalkylsulfonate anion.

13. The composition of claim 1 wherein the organic ion pair compound comprises a fluoroalkylsulfonylimide anion.

14. The composition of claim 1 wherein the organic ion pair compound comprises a phosphinate anion.

15. The composition of claim 1 wherein the organic ion pair compound comprises a tetrafluoroborate or a tetraarylboride anion.

16. A smectic liquid crystal composition for use in a smectic liquid crystal display device, comprising an organic ion pair compound comprising an anion and a cation, wherein resistivity of the composition including the organic ion pair compound is in the range of about 140 MΩ·cm to about 20 GΩ·cm.

17. A smectic liquid crystal composition for use in a smectic liquid crystal display device, comprising an organic ion pair compound comprising an anion and a cation, wherein resistivity of the composition including the organic ion pair compound is in the range of about 140 MΩ·m to about 3 GΩ·cm.

18. The composition of claim 1 wherein a concentration of about 0.1 wt % of the organic ion pair compound in the composition produces a resistance of about 14 kΩ to about 2 MΩ in a ferroelectric liquid crystal display cell of about 1 cm$^2$ area, wherein the layer comprising the liquid crystal is of a thickness of about 1 μm.

19. The composition of claim 18 wherein a concentration of about 0.1 wt % of the organic ion pair compound in the composition produces a resistance of about 14 kΩ to about 0.3 MΩ in a ferroelectric liquid crystal display cell of about 1 cm$^2$ area, wherein the layer comprising the liquid crystal is of a thickness of about 1 μm.

20. A smectic liquid crystal composition for use in a smectic liquid crystal display device, comprising an organic ion pair compound comprising an anion and a cation, wherein the organic ion pair compound, comprising an anion and a cation, is of any of the following compounds:

or any mixture thereof.

21. A ferroelectric liquid crystal display device comprising the composition of claim 1.

22. A ferroelectric liquid crystal display device comprising an ion pair compound comprising any anion of any of the compositions of claim 20 in combination with any of cation of any of the compositions of claim 20, provided the cation and the anion together have sufficient solubility in the liquid crystal composition such that resistivity of the composition including the organic ion pair compound is in the range of about 140 MΩ·cm to about 20 GΩ·cm.

23. The display device of claim 21 wherein the display operates on a non-DC balanced algorithm with a greater than 50% duty cycle with a lower level of image sticking relative to a comparable display lacking the organic ion pair compound.

24. The display device of claim 23 wherein the display is brighter when in operation than is a comparable display lacking the organic ion pair compound and operating on a duty cycle of 50% or less.

25. The display device of claim 21 comprising a ferroelectric liquid crystal layer having a composition wherein resistivity of the composition including the organic ion pair compound is in the range of about 140 MΩ·cm to about 20 GΩ·cm.

26. The display device of claim 21 comprising a ferroelectric liquid crystal layer having the composition wherein resistivity of the composition including the organic ion pair compound is in the range of about 140 MΩ·cm to about 3GΩ·cm.

27. The display device of claim 21 wherein image sticking persists for less than about $1/30^{th}$ of one second.

28. The display device of claim 21 wherein image sticking persists for less than about $1/12^{th}$ of one second.

29. The display device of claim 21 wherein the ferroelectric liquid crystal composition comprises any of the following compounds:

-continued

-continued or any mixture thereof.

30. The display device of claim 20 wherein the ferroelectric liquid crystal composition comprises a quaternary ammonium or a quaternary phosphonium.

31. The display device of claim 20 wherein the ferroelectric liquid crystal composition comprises a sulfonate, phosphinate, or bis-sulfonylimide anion.

32. A method of reducing image sticking in a ferroelectric liquid crystal composition used in a ferroelectric liquid crystal display device, comprising adding an organic ion pair compound to the composition.

33. The method of claim 32 wherein the organic ion pair compound is present at about 0.005 wt % to about 0.5 wt %, or at about 0.05 wt % to about 0.15 wt %.

34. The method of claim 32 wherein addition of a suitable amount of the organic ion pair compound to the composition results in a composition resistivity of about 140 MΩ·cm to about 20GΩ·cm.

35. The method of claim 34 wherein addition of a suitable amount of the organic ion pair compound to the composition results in a composition resistivity of about 140 MΩ·cm to about 3GΩ·cm.

36. The method of claim 32 wherein the organic ion pair compound comprises any of the following compounds:

or any mixture thereof.

37. The method of claim 32 wherein the organic ion pair compound comprises any anion of any of the following compounds in combination with any of the cations of the following compounds:

or any mixture thereof.

* * * * *